United States Patent
Dufay (10) Patent No.: US 8,835,708 B2
(45) Date of Patent: Sep. 16, 2014

(54) APPARATUS FOR BODY TREATMENT CONSISTING OF A SHELL MADE OF AT LEAST TWO COMPLEMENTARY PORTIONS

(76) Inventor: Francois Dufay, Loulle (FR)

(*) Notice: Subject to any disclaimer, the term of this patent is extended or adjusted under 35 U.S.C. 154(b) by 511 days.

(21) Appl. No.: 13/056,109

(22) PCT Filed: Jul. 30, 2008

(86) PCT No.: PCT/EP2008/060013
§ 371 (c)(1),
(2), (4) Date: Jan. 26, 2011

(87) PCT Pub. No.: WO2010/012302
PCT Pub. Date: Feb. 4, 2010

(65) Prior Publication Data
US 2011/0130713 A1    Jun. 2, 2011

(51) Int. Cl.
*A61F 5/00*    (2006.01)
(52) U.S. Cl.
USPC .............................................. 602/42; 602/12
(58) Field of Classification Search
USPC ......................................... 602/41–54, 5, 12
See application file for complete search history.

(56) References Cited

U.S. PATENT DOCUMENTS

| | | | |
|---|---|---|---|
| 4,003,371 A | 1/1977 | Fischer | |
| RE29,517 E * | 1/1978 | Becker | 52/144 |
| 4,432,354 A | 2/1984 | Lasley | |
| 4,447,504 A | 5/1984 | Goebel | |
| 5,000,164 A | 3/1991 | Cooper | |
| 5,038,769 A | 8/1991 | Krauser | |
| 2009/0260711 A1* | 10/2009 | Alder et al. | 141/39 |
| 2010/0083417 A1* | 4/2010 | Alder et al. | 2/69 |

FOREIGN PATENT DOCUMENTS

| | | |
|---|---|---|
| EP | 0008719 | 3/1980 |
| EP | 0 325 771 | 8/1989 |
| EP | 1089698 | 4/2001 |
| EP | 1 170 033 | 1/2002 |
| FR | 2 544 202 | 10/1984 |
| GB | 1 352 142 | 5/1974 |
| WO | WO 01/93790 | 12/2001 |

OTHER PUBLICATIONS

International Search Report for Application No. PCT/EP2008/060013 (8 page).

* cited by examiner

*Primary Examiner* — Michael A. Brown
(74) *Attorney, Agent, or Firm* — Kevin R. Erdman; Brannon Sowers & Cracraft PC (57) ABSTRACT

Apparatus formed by a shell that may be placed around a part of the body, wherein said shell comprises:
- an inlet that may be connected to a gas source and an outlet to evacuate the gases present inside the shell;
- at least two complementary portions defining between them a cavity with a cross section that is larger than that of the part of the body to be treated, characterized in that
the walls of the two complementary portions have an average heat conduction that is lower than 65 mW/m·K measured according to EN-12667.

20 Claims, 6 Drawing Sheets

APPARATUS FOR BODY TREATMENT CONSISTING OF A SHELL MADE OF AT LEAST TWO COMPLEMENTARY PORTIONS

CROSS-REFERENCE TO RELATED APPLICATION

This application is a National Stage filing, under 35 U.S.C. §371, of International Application Serial No. PCT/EP2008/060013, filed Jul. 30, 2008 and designating the United States, the entire disclosure of which is expressly incorporated herein by reference.

BACKGROUND OF THE INVENTION

1. Field of the Invention

The invention relates to the field of body treatment, topical or systemic, curative or preventive, in therapeutic, aesthetics and cosmetic fields for humans and animals and more particularly the treatment of open wounds.

2. Background of the Background Art

The usual treatment of open wounds consists of applying dressings onto the wound. The problem that is raised is that of the contact between the dressing and the wound, and the risks of the proliferation of microbes.

In order to overcome this disadvantage, several variants of devices for treating wounds or any injury or sickness of part of the body of a patient by exposing this part to fluid have been proposed. In general, these devices comprise at least one wall forming a chamber or a sealed cavity more or less hermetically around the part of the body to be treated, and which comprise means of injecting a treatment fluid into the chamber so that it comes into contact with said part of the body to be treated, and means of evacuating fluids from this chamber. In this field, examples such as the U.S. Pat. No. 4,003,371, EP 0 008 719, U.S. Pat. No. 4,432,354, U.S. Pat. No. 4,447,504 and EP 1 089 698 may be mentioned.

In the field of the treatment of burns and hypothermia, similar devices to those mentioned above many be cited, such as WO 01 93 790 or U.S. Pat. No. 5,000,164, wherein the general principle of the device is identical, only the fluids used, the pressure, temperature, pH, etc. in the chamber vary according to the type of treatment and according to the part of the body to be treated. Of course, the form of the device also varies according to whether the part of the body to be treated is a leg, an arm, a neck, a torso, etc.

Regardless of the type of treatment to be applied to a part of the body, the control of the atmosphere inside de the chamber is very important. In particular, the temperature must be controlled, as the temperatures window of the treatment is generally very narrow due to the fact that the body, especially if injured, may not be exposed for long periods to wide temperature ranges and also that the active principles used (therapeutic substances, essential oils, etc.) are also temperature sensitive and may be damaged or lose their efficiency with the temperature. Furthermore, in therapeutic fields, it is important to control the temperature in order to limit or even prevent the aerobic or anaerobic bacterial proliferation. The advantage of devices such as those described above is precisely that they may be used almost anywhere and any time, as the ambient temperature around the chamber may vary enormously from one treatment to another, which may have negative consequences on the reproducibility of the treatment. It is obvious that by increasing the flow of fluid through the chamber, the absolute temperature may be relatively controlled, but at the cost of a drop in the temperature perceived by the person being treated, which may become uncomfortable. Furthermore, according to the active principle used, this solution may become very costly.

None of the devices described above deal with this problem of controlling the temperature in the chamber. It therefore remains in the art a problem to be solved.

BRIEF DESCRIPTION OF THE INVENTION

The invention is defined in the independent claims below. Preferred variants are defined in the dependent claims. The purpose of the invention is to propose an improved treatment apparatus which permits active principles to be fed to the surface of a part of the body, human or animal, whilst preserving as far as possible any contact with the part to be treated and whilst offering better control of the conditions around the part being treated, especially the thermal conditions. Its aim is to maintain a climate that is favourable to the treatment applied, for example the healing of a wound, by avoiding major temperature changes around the part being treated. A treatment according to the invention is less painful as it avoids the contact between the wound and the exudates produced by the wound, and provides an environment that is favourable to healing.

For this purpose, the invention relates to, according to its most widespread sense, an apparatus composed of a shell that may be placed around a part of the body, wherein said shell comprises:

(a) an inlet that may be connected to a gas source and an outlet to evacuate the gases present inside the shell;

(b) at least two complementary portions defining between them a cavity with a cross section that is larger than that of the part of the body to be treated and in which, (c) the walls of the two complementary portions have an average heat conduction that is lower than 65 milliWatts per meter·K (mW/m·K) measured according to EN-12667.

According to the invention, it is essential that the shell is formed by at least two complementary portions in a thermally insulating material.

Preferably, the apparatus comprises two complementary shells which have a substantially cylindrical, tapered or prismatic form. The shell may have a first open frontal end and a second closed frontal end or the two ends may be open, wherein the open ends may each comprise one or several orifices. In the case where there are several orifices in one end, they may be connected to a single chamber or, on the contrary, be connected to several corresponding distinct compartments, included in the shell. The different geometrical variants of the shell, and the number of compartments in the shell depend on the part of the body to be treated and the type of treatment to be applied.

In order to preserve optimally the conditions inside the cavity formed by the shell, in particular as concerns the temperature, the shell is composed of materials which permit its average heat conduction to be reduced to less than 65 mW/m·K measured according to EN-12667, preferably to less than 45 mW/m·K, or even 40 mW/m·K.

To reach such values of thermal insulation, the shell is advantageously formed of impermeable cellular materials, for example an expanded polypropylene (PPE), an expanded polystyrene (PSE), expanded polyurethane (PUE) or any other expanded material which has the thermal, structural and compatibility properties required by the application to which the apparatus of the invention is designed. For example a PPE with a density between 20 and 60 grams per liter (g/l) typically has a heat conductivity of around 38 to 42 mW/m·K, and a PSE with a density between 19 and 30 g/l typically has a heat conductivity of around 36 to 39 mW/m·K.

According to one specific embodiment, said material has a treatment to smooth the surface to make it easier to clean by heat treatment (firing or glazing) or by the application of applied and draped films which form a skin on the internals and/or external surfaces of the material.

Alternatively, or in combination with cellular materials, fibrillar materials may also be used, such as mineral fibres (for example, glass fibres, or rock) or polymers (for example, polyethylene, polypropylene). Glass wool typically has a heat conductivity of around 34 to 65 mW/m·K, whereas rock wool is around 38 to 47 mW/m·K.

For structural, fluid sealing and hygiene reasons, the fibrillar material is generally positioned between two skins to form a sandwich. The skins may be flexible or rigid according to the type of application. Preferably the shell is structurally self-supporting and therefore rigid skins are preferred. If the thermal insulation is sufficient, the fibres may be impregnated with resin to form a composite material.

Advantageously, the shell further has, on each frontal opening, means of connection with the surface of the member. Preferably, said means of connection are formed by a sleeve that may be connected to one of its ends to the periphery of one opening of the shell, and to the other end to come into contact with the body. According to one variant, said means of connection is composed of an inflatable ring which engages with the surface of said shell. Such means of connection—or any other equivalent means—permit the thermal conditions in the cavity formed by the shell to be maintained optimally.

According to one specific embodiment, at least one of the parts has means of supporting the part of the body surrounded by the shell. For example, said supporting means are formed by transversal straps. According to one alternative, one of the shells forming the shell has pins to anchor said transversal straps, wherein said anchoring pins are preferably divisible or removable. Advantageously, said anchoring pins are formed by protruding parts provided on the edge of the shell, and in that the complementary shell has recesses that are complementary to these protruding parts.

According to another variant, said supporting means is formed by transversal cradles. According to one variant, said supporting means are formed by pads engaging with the base of one of the shells.

According to one specific embodiment, the shell is formed by two shells that may or not be articulated by a hinge. For example, the shell may be formed by two independent shells, wherein one of the shells has means of accommodating the other shell in the open position. Advantageously, one of the shells has on its edge at least one complementary rib with at least one groove provided on the complementary shell, to create a baffle.

Preferably, one of the shells has a groove to accommodate a gas pipe. According to a specific embodiment, at least one part of the connection of a gas pipe of the apparatus is formed by a plate extended by a tubular end, wherein said plate engages with a complementary housing provided in the shell.

The apparatus according to the invention features a system for supplying at least one active principle, wherein the latter may be in gas, liquid or solid (particles) form and advantageously transported by a carrier gas. According to one variant, it features a gas supply system comprising a means of enriching a carrier gas with at least one active principle. According to another variant, it further features a gas supply system comprising a vaporisation chamber to enrich a carrier gas with an active principle.

According to another variant, it further features a gas supply system comprising a mixer to enrich a carrier gas with at least one liquid or solid active principle packaged in a container connected to the supply system.

According to one specific embodiment, it further comprises at least one gas supply tank. Preferably, the gas supply system comprises means of regulating the hygrometry and/or the temperature and/or the pH and/or the flow rate and/or the physical and chemical characteristics of the gas injected.

Advantageously, said gas supply system comprises means of treating gases at the outlet of the shell. According to one embodiment, said means of treating gases comprise a gas cleaner, connected to a vacuum generator. According to one variant, it further comprises a system for connecting the inlet of the shell to a vacuum generator to establish a pressure in the shell that is lower than atmospheric pressure.

Preferably, the shell has at least one transparent window.

According to one specific embodiment, the shell has an opening which extends towards the interior by a sleeve to allow operations to be carried out inside the chamber formed by the two shells. According to another variant, it features at least one physical-chemical sensor to analyse the atmosphere in the chamber formed by the two shells. Preferably, the apparatus features means of locking the two shells. Advantageously, at least one of the shells incorporates a radio-frequency label.

BRIEF DESCRIPTION OF THE DRAWINGS

The invention will be more clearly understood upon reading the following description, in reference to the appended drawings wherein.

DETAILED DESCRIPTION OF THE EMBODIMENTS OF THE INVENTION

The invention will be described below in reference to a non-restrictive example of an embodiment.

Figure 1:
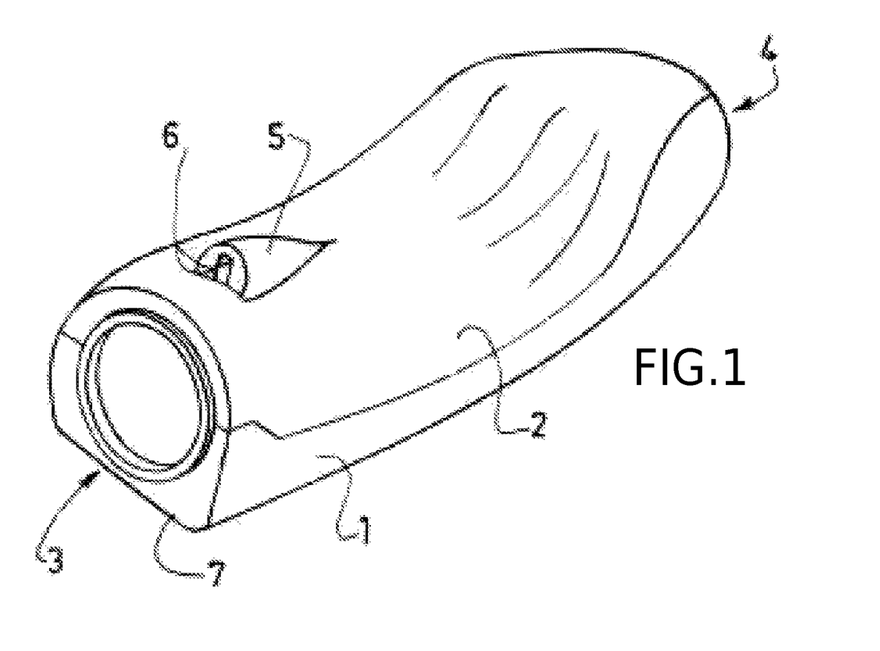
FIG. 1 shows a perspective view of an embodiment of an apparatus according to the invention.

FIG. 1 shows a perspective view of an embodiment of an apparatus according to the invention. It is in the form of a rigid shell formed by two shells (1, 2) connected to one another to form a chamber inside of which may be held part of the body, for example a leg or an arm. The shells (1, 2) have, in the example described, an elongated form, with an open first frontal end (3) and a second closed frontal end opposite (4). The upper shell (2) has a protruding part (5) which opens onto a gas inlet (6) that is connected to the inside of the chamber defined by the shells (1, 2). A groove (7) provided on the lower surface of the shell (1) is designed to accommodate the gas supply tube.

Figures 2A, 2B:
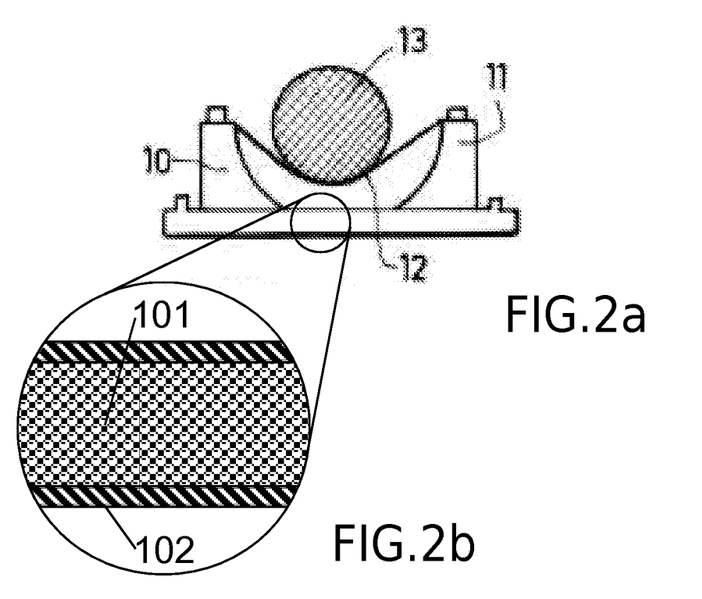
FIGS. 2a and 2b show views of the lower shell according to a transversal cross sectional plane with a detail of a wall comprising a core made of cellular material sandwiched between two skins.

As illustrated in FIG. 2b, the two shells (1, 2) may be formed of an expanded material (101), for example expanded polypropylene or expanded polystyrene. They may have undergone a surface treatment (102) which permits the gaseous diffusion through the wall to be limited, to ensure a certain hygiene, to reinforce the system structurally, and/or to give it a pleasant appearance. The surface treatments which are possible include for example (a) glazing, by which the surface of the cellular material is smoothed by applying heat treatment and, optionally, a mechanical treatment of the surface or (b) the application of a skin on one or both faces of the walls of the shells. The materials used for the skins vary according to the function(s) they have: barrier, hygiene, structural or aesthetic.

For example, for gas barrier effects, multi-layer films of which the outer layers have a function of adhering to the support and weldability whereas the inner layer(s) have a function of providing a barrier to the gases. By using films of the types polyethylene/ethylene vinyl alcohol/polyethylene (PE/EVOH/PE) or polystyrene/ethylene vinyl alcohol/polystyrene (PS/EVOH/PS) or similar, values of permeability to gases may be obtained that are very low. It may also be envisaged to use metal foils, such as aluminium foil. The hygiene of the system will be made easier by the application of smooth skins that are not very adherent, such as certain polymers with low surface energy such as polyethylene (PE, HDPE), polypropylene (PP), polyoxomethylene (POM), polytetrafluorethylene (PTFE), etc. For structural applications, more rigid materials, such as metals, structural polymers (epoxy, polyesters, etc.), composites reinforced with fibres, etc. can do the job. Finally, for the aesthetic appearance, a leather finish, or any other texture on the outer surface may be applied by familiar techniques by a person skilled in the art, or on the contrary a smooth surface may also be obtained using techniques developed for example in the automobile industry or with sports apparatuses. Providing that the average thermal insulation of the shell remains adequate, one of the shells may have a transparent window which permits the progress of the wound to be observed, and to apply radiation treatments. A double-glazed system may be used in order to reduce the heat conduction of the window and thus furthermore make possible a large sized window without losing the thermal properties and by reducing the thermal gradients.

In the case of skins being applied to the surface of the insulating material, the considerations of the adhesion of said skins to the insulating material must be taken into account. In particular, it may prove difficult to find materials that adhere suitably to materials such as polypropylene, whether it is expanded or in fibre form. In this case, it may be advantageous to use a material for the skins that is compatible, or even of the same nature as the material which forms the core of the wall. In the case of expanded polypropylene, for example, the application of polypropylene skins is particularly preferred.

It is clear that a surface treatment of the cellular or fibrillar materials which form the shell of the apparatus of the invention must advantageously provide an improvement of the gas barrier properties, as if the permeability of the walls to gases is too high, this would cause the consumption of gas to rise unacceptably and, more especially, that of the active principle, as well as a heat transfer which would cancel out the effects sought by the use of these thermally insulating materials. Indeed, a material such as expanded polypropylene generally offers a permeability, measured according to ASTM F1927-98, of around 1000 to 10.000 centimeter cubed per meter squared·atmosphere·24 hour ($cm^3/m^2 \cdot atm \cdot 24$ h) according to the density and thickness of the material, which is insufficient for most of the applications targeted by the invention. This permeability may be reduced by the application of polypropylene skins for example, with values below 600 and even 300 $cm^3/m^2 \cdot atm \cdot 24$ h according to the grade and the thickness of the film. Values of below 200, 100 and in the case of specific barrier materials, with which a person skilled in the art is familiar, below 10 and can even reach 1 $cm^3/m^2 \cdot atm \cdot 24$ h may be achieved.

FIG. 2a shows a view of the lower shell according to a transversal cross sectional plane. The lower shell (1) has side posts (10, 11) which are stood perpendicularly to the base. These posts support straps (12) which extend transversally, to support the member (13) that is enclosed between the two shells (1, 2).

Figure 3:
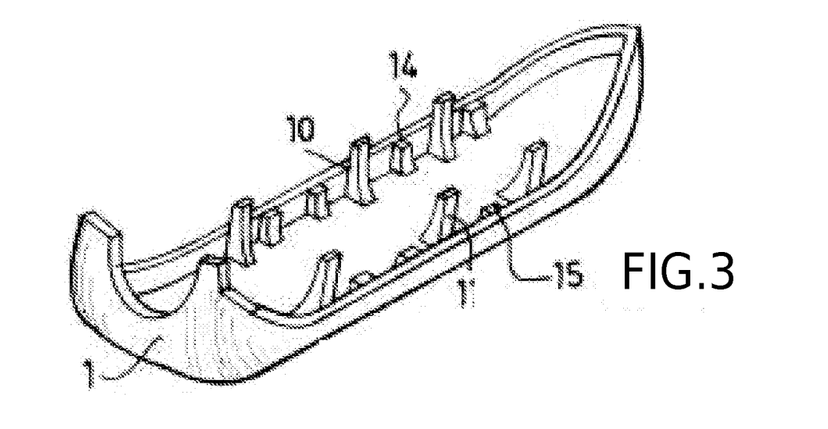
FIG. 3 shows a view of the inside of the lower shell.

FIG. 3 shows a view of the inside of the lower shell. The lower shell (1) has the general appearance of a flat bottomed tray. The posts are distributed over one part of the length of the shell, on either side of the central part. The pins are divisible or removable, and those which are not used to support a transversal strap are cut off or removed (14, 15). The strap has at each end a series of holes designed to accommodate the tubular end of the pins, and which permit the adjustment of the tension and the position of the member.

Figure 4A:
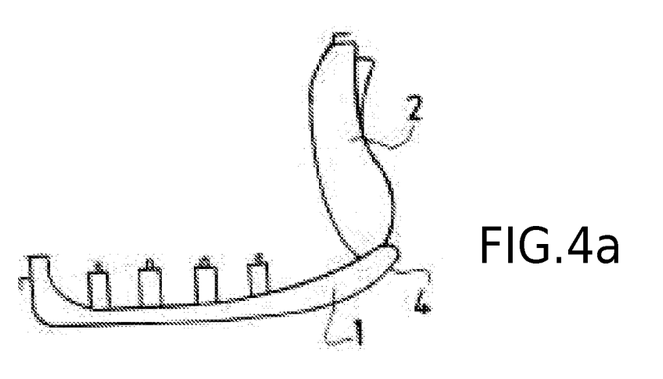
FIGS. 4a and 4b show two views of the apparatus in the open position.
Figure 4B:
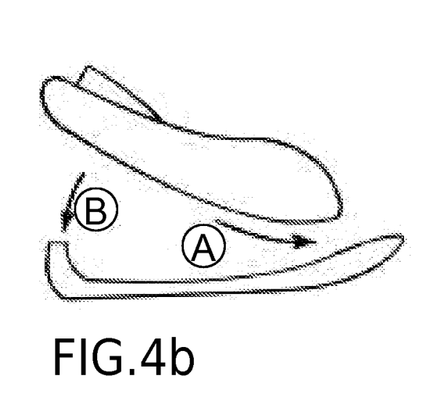

FIG. 4 shows two views of the apparatus in the open position. The lower shell (1) has on its end (4) a housing which can accommodate the end of the upper shell (2) when the apparatus is open (FIG. 4a). This solution allows the upper shell (2) to be held without it coming into to contact with non-sterile surfaces. To close the shell, the upper shell (2) just needs to be closed down onto the lower shell (1) in two successive movements (A) and (B) (FIG. 4b).

Figure 5:
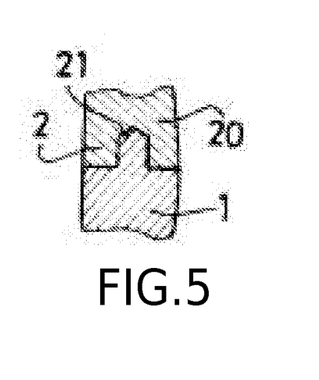
FIG. 5 shows a detailed view of the connection between the two shells

FIG. 5 shows a detailed view of the connection between the two shells. One of the shells (1) has on its edge a peripheral protrusion (20) that is complementary to a peripheral rib (21) provided on the edge of the complementary shell (2), in order to create a baffle to improve the closing and the seal.

Figure 6:
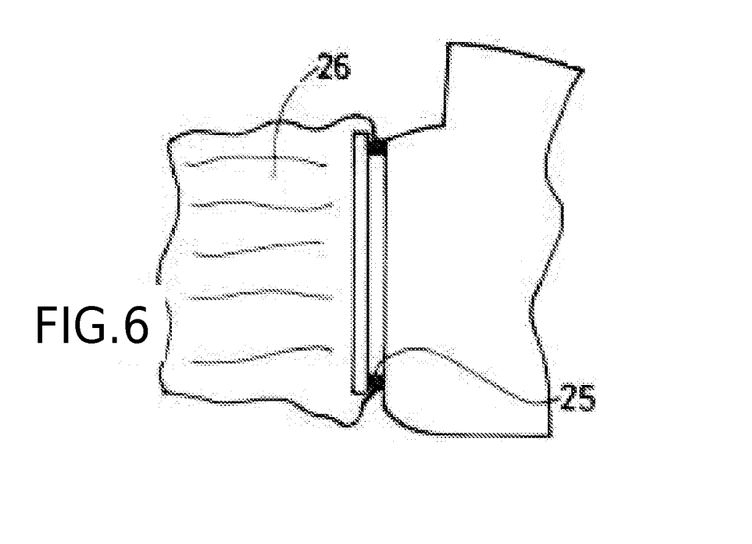
FIG. 6 shows a detailed view of the open end of the apparatus.

FIG. 6 shows a detailed view of the open end of the apparatus. It has an annular groove (25) to clamp the end of a flexible sleeve (26). This flexible sleeve has at least one part made of an elastic material. It provides an impervious seal around the member being treated, in a zone that is remote from the wound or the zone being treated.

Figure 7:
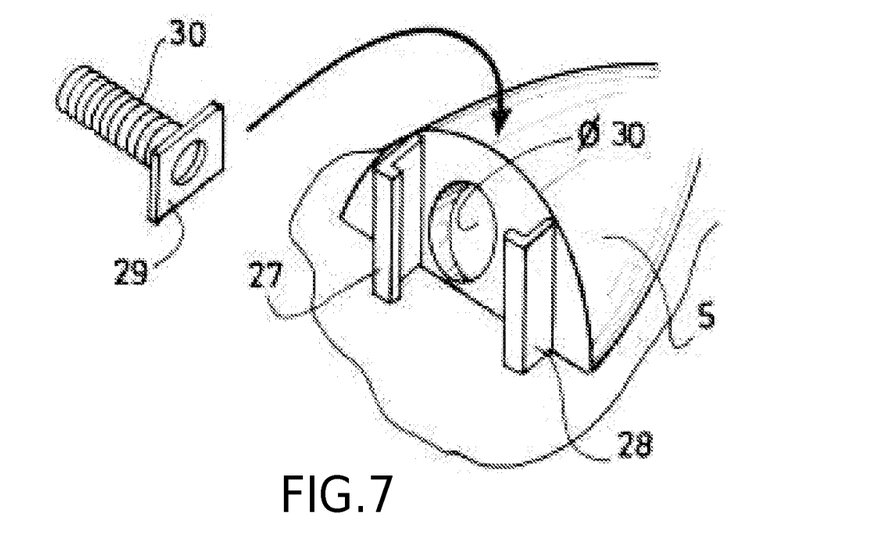
FIG. 7 shows a detailed view of the connection between the fluid inlet and the shell.

FIG. 7 shows a detailed view of an example of connection between the fluid inlet and the shell. The protruding part (5) has two hooks (27, 28) which permit the flange (29) of a nozzle (30) to be introduced, onto which the gas inlet tube is mounted. Any other means of connection of a fluid source to the shell that is quickly fitted and removed and impervious may of course be used in the invention.

Figure 8:
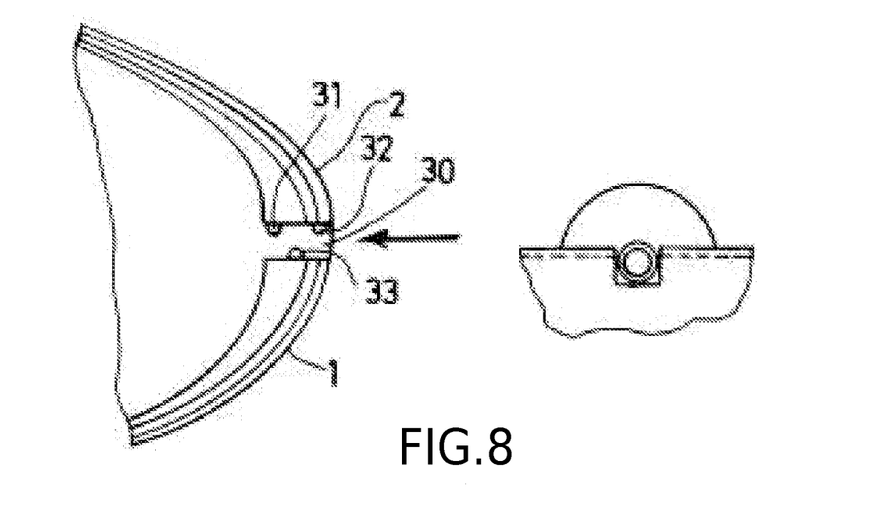
FIG. 8 shows a cross sectional view of the closed end of the apparatus.

FIG. 8 shows a cross sectional view of the closed end of the apparatus. The two shells (1, 2) define between them an opening (30) of which the cross section substantially corresponds to an outlet tube. The surface of the shells has hooks (31 to 33) which hold the tube once it has been engaged in the hole (30).

Figures 9, 10:
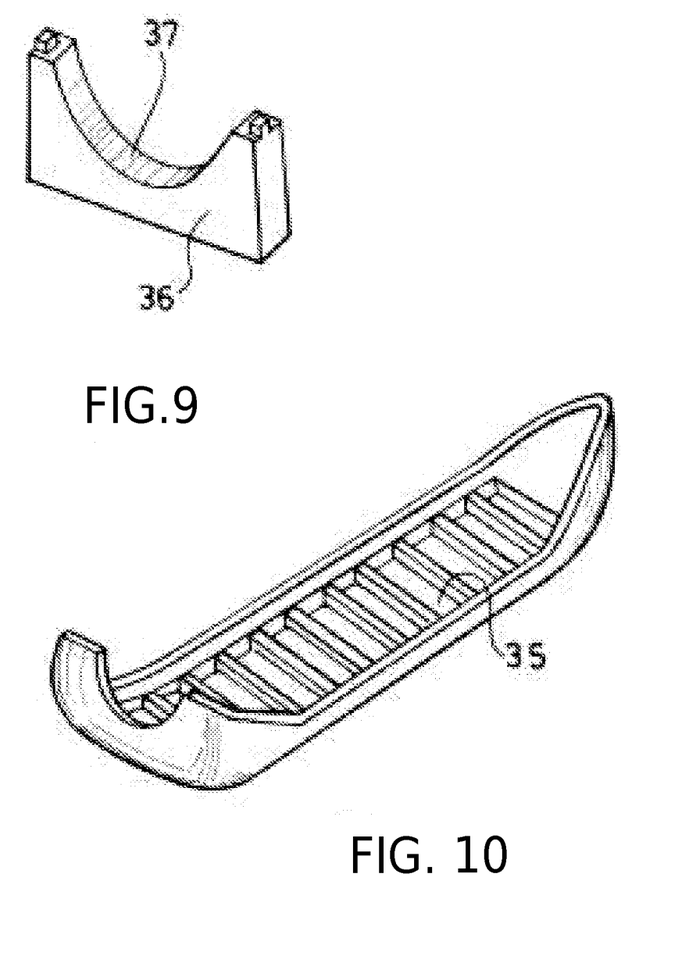
FIGS. 9 and 10 show views of one variant of embodiment.

FIGS. 9 and 10 show views of one variant of embodiment. The lower shell (1) has slots (35) to accommodate cradles (36) with a semi-circular shaped cut-out. These cradles are positioned at determined intervals to hold the member whilst avoiding the injured zones.

Figure 11:
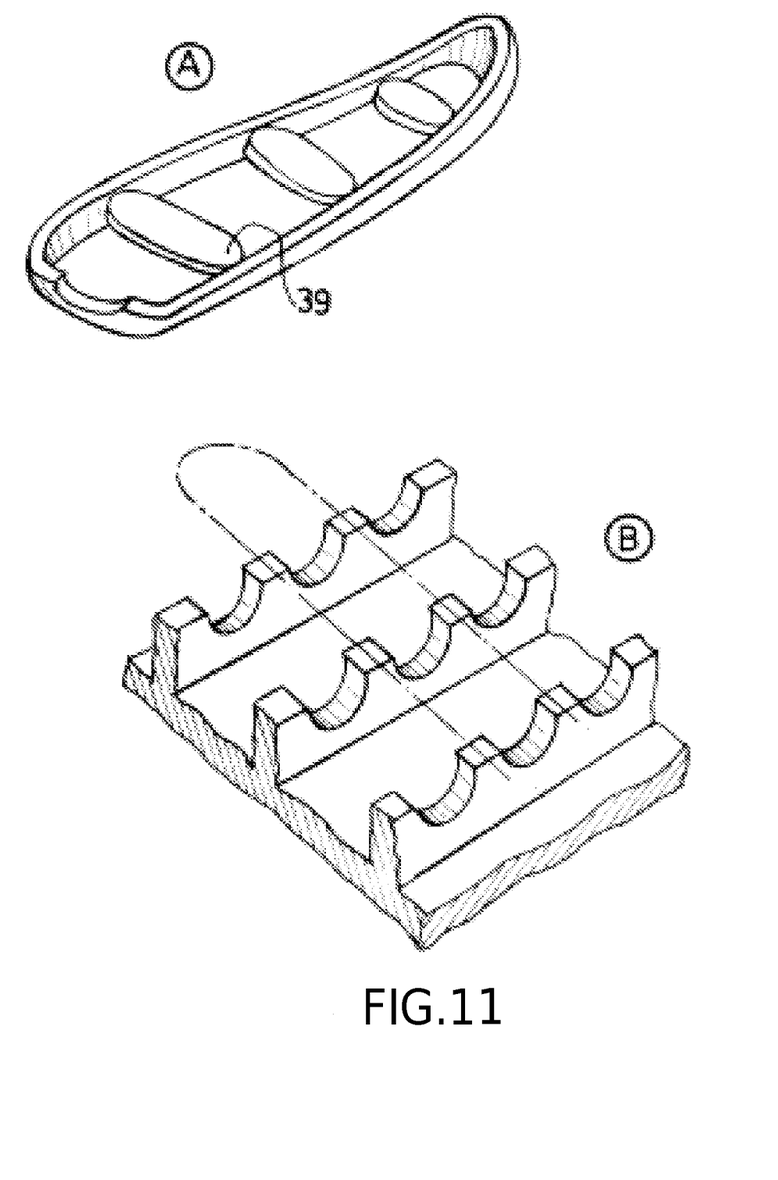
FIG. 11 shows a view of another variant of embodiment.

FIG. 11 shows a view of another variant of embodiment. In this solution, the base of the shell (1) accommodates inflatable pads (39) which support the member inserted in the chamber.

In the case of treatments that last a long time, it is perhaps advantageous to permit the member being treated to move, especially if it has a joint. In this case, the apparatus may comprise several adjacent sections on the shell that are relatively rigid connected to one another by flexible sections or by a hinge to allow the movement of the joint of the part of the body treated. Another solution to this problem is that the shell is larger at the position of the joint of a member.

The apparatus of the invention may be advantageously used in a large number of surface treatments of a part of the body, either in the therapeutic, health care and "wellness", or cosmetic fields.

In the therapeutic field, the treatment of open wounds may be mentioned, or skin diseases, wet wounds such as for example burns, venous or lymphatic wounds, or hypothermia. By health care, it is meant what are usually classed as alternative medicines, comprising oil treatments, especially essential oils, Bach flowers, frankincense, hot vapours or cold treatments. Finally, the cosmetic treatments comprise a multitude of applications, such as the lightening of dark skins, the pigmentation of light skins, the bleaching of hair, the treatment of skin rashes, the removal of scars or marks, hydrating treatments, anti-ageing care, sun preparation, etc.

To carry out such treatments, the part of the body to be treated is simply placed between the at least two complementary elements of the shell as described above, to connect a point of the cavity formed by said shell to a source of a mixture of at least one carrier gas and at least one principle which has a therapeutic, health care or cosmetic activity on the part of the body treated and another point of said cavity to a gas outlet, and to inject into the cavity containing the part of the body to be treated said mixture of at least one carrier gas and at least one active principle.

The gas flow may be continuous, but in certain cases, it may be discrete, filling the cavity with a predetermined quantity of gas and active principle, then sealing the gas inlet and outlet and letting the active principle act on the part of the body being treated. After a time for the action, the cavity may be purged and may be replaced by a new dose of active principle. The pressure in the cavity may vary according to the applications, either lower or higher than the atmospheric pressure. It is also possible to vary the pressure during the treatment, for example, to stimulate the circulation which may increase the receptivity of the part of the body treated to the effects of the active principles used.

The invention claimed is:

1. An Apparatus composed of a shell that may be placed around a part of a body, wherein said shell comprises:
   (a) an inlet structured and arranged to be connected to a gas source and an outlet to evacuate gases present inside the shell;
   (b) at least two complementary portions defining between them a cavity with a cross section that is larger than that of the part of the body to be treated,
   wherein
   (c) a plurality of walls of the at least two complementary portions has an average heat conduction that is lower than 65 mW/m·K, and
   (d) the at least two complementary portions are formed from a cellular material having an internal surface and an external surface that have undergone a surface treatment that is one of a heat treatment smoothing type and an application of surface skins.

2. Apparatus according to claim 1 where the at least two complementary portions are a first shell and a second shell which have a general form that is selected from the group consisting of substantially cylindrical, tapered and prismatic, of which at least one end of the first and second shells comprises at least one opening equipped with means permitting the apparatus to be sealed around the part of the body being treated.

3. Apparatus according to claim 1 where the heat conduction is lower than 50 mW/m·K.

4. Apparatus according to claim 1 where the cellular material is one of expanded polypropylene and expanded polystyrene.

5. Apparatus according to claim 1 of which the walls have a permeability to oxygen between 1 and 300 $cm^3/m^2 \cdot atm \cdot 24$ h.

6. Apparatus according to claim 1 in which a plurality of adjacent sections of the shell are connected to one another by at least one of a plurality of flexible sections and a hinge to permit the movement of a joint of the part of the body being treated.

7. Apparatus according to claim 1 further featuring a gas supply comprising a means of enriching a carrier gas with at least one active principle.

8. Apparatus according to claim 7 further comprising means of controlling at least one of the following properties: temperature, hygrometry, pH, gas flow, composition of the gas injected into the cavity of the shell, and drop in pressure in the cavity, wherein said means are used to maintain each of these properties at predetermined levels and, in the case of excessive deviation from one of these properties, to trigger an alarm or to stop the apparatus.

9. Apparatus according to claim 1 wherein the cavity includes means for supporting the part of the body to be treated.

10. Apparatus according to claim 1 where the two complementary portions comprise a fibrillar material having at least one of a plurality of mineral fibres and a plurality of polymeric fibres.

11. Apparatus according to claim 7 for therapeutic treatment of at least one of open wounds, skin diseases, wet wounds, venous wounds, and lymphatic wounds.

12. A Method for cosmetic treatment of a part of the body comprising the following steps:
   a) Insertion of the part of the body to be treated between two complementary elements forming a shell around said part, wherein said elements are formed from a material with heat conduction lower than 65 mW/m·K;
   b) Connecting a point of a cavity formed by said shell to a source of a mixture of at least one carrier gas and at least one principle for at least one of the cosmetic treatments selected from the group consisting of lightening dark skins, pigmentation of light skins, bleaching hair, treating skin rashes, removing scars, removing marks, hydrating treatment, anti-ageing care, and sun exposure preparation on the part of the body treated, and connecting another point of said cavity to a gas outlet; and
   c) Injecting into the cavity containing the part of the body to be treated said mixture of at least one carrier gas and at least one active principle.

13. The method of claim 12, further comprising the step of using an apparatus for at least one of the cosmetic treatments of the part of the body, the apparatus comprising a shell that may be placed around the part of the body, wherein said shell comprises an inlet connected to a gas source and an outlet to evacuate gases present inside the shell; and at least two complementary portions defining between them a cavity with a cross section that is larger than that of the part of the body to be treated, wherein a plurality of walls of the two complementary portions has an average heat conduction that is lower than 65 mW/m·K measured according to EN-12667, and the two complementary portions are formed from a cellular material having an internal surface and an external surface that have undergone a surface treatment that is one of a heat treatment smoothing type and an application of surface skins.

14. The apparatus of claim 1, wherein the heat conduction is lower than 45 mW/m·K.

15. The apparatus of claim 1, wherein the heat conduction is lower than 40 mW/m·K.

16. The apparatus of claim 5, wherein the walls have a permeability to oxygen between 10 and 200 $cm^3/m^2 \cdot atm \cdot 24$ h.

17. The method of claim 13, further comprising the step of supporting the part of the body to be treated within the cavity.

18. The method of claim 13, further comprising the step of controlling at least one of the following properties within the cavity: temperature, hygrometry, pH, gas flow, composition of the gas injected into the cavity of the shell, and drop in pressure in the cavity.

19. The method of claim 18, wherein the controlling step includes providing means for maintaining each of the properties at predetermined levels and, in the case of excessive deviation from at least one of the predetermined levels of the properties, to trigger an alarm or to stop the apparatus.

20. The method of claim 13, wherein the step of using an apparatus includes the plurality of walls of the two complementary portions having an average heat conduction that is lower than 50 mW/m·K, measured according to EN-12667.

\* \* \* \* \*